United States Patent [19]
Vona

[11] Patent Number: 5,527,352
[45] Date of Patent: Jun. 18, 1996

[54] TIME FOCUSED INDUCTION OF PREFERENTIAL NECROSIS

[76] Inventor: Matthew J. Vona, 7911 Bonnydowns Way, Elk Grove, Calif. 95758

[21] Appl. No.: 286,671

[22] Filed: Aug. 5, 1994

[51] Int. Cl.⁶ ..................................................... A61N 5/00
[52] U.S. Cl. ............................................. 607/100; 600/10
[58] Field of Search ................................... 607/100–102, 607/115, 154; 600/10

[56] References Cited

U.S. PATENT DOCUMENTS 4,230,129  10/1980  LeVeen ..................................... 607/154
5,010,897   4/1991  LeVeen ..................................... 607/101

FOREIGN PATENT DOCUMENTS 2370483  6/1978  France ..................................... 607/154

Primary Examiner—Lee S. Cohen
Attorney, Agent, or Firm—James M. Ritchey

[57] ABSTRACT

A non-ionizing radiation emitting apparatus and method of use for preferentially inducing cellular necrosis in abnormal cells has a non-ionizing radiation generator with opposing plates or poles. A time focused electromagnetic field with sufficient energy to cause either electroporation or electromagnetic enzyme interference of the abnormal cells is included and functions by rotating the generated radiation about a central axis thereby focusing the radiation at a desired location containing at least a portion of the abnormal cells.

20 Claims, 2 Drawing Sheets

FIG. — 1

TIME FOCUSED INDUCTION OF PREFERENTIAL NECROSIS

BACKGROUND OF THE INVENTION

1. Field of the Invention

A method of producing selectively induced (or preferential) necrosis in selected tissues or cells is described. More specifically, the preferential necrosis is generated by employing low energy electric fields that are focused at the target cells or cell groups.

2. Description of the Background Art

Various methods exist for killing abnormal cells. However, few, if any, reliable radiological methods exist for eliminating abnormal cells (lymphoma cells and the like) found in close proximity to, or buried within, normal cells without causing significant damage to non-targeted cells. Based on the unusual sizes and shapes of many abnormal cells, compared with normal cells, the subject method selectively induces necrosis in abnormal cells.

The morphological characteristics of a cell's membrane influence transcellular voltage distributions (Eberhard Neumann, Arthur E. Sowers, and Carol A. Jordan, "Electroporation and Electrofusion in Cell Biology," Plenum Publishing Company, New York, N.Y., 1989; Christine E. Miller and Craig S. Henriquez, "Three-Dimensional Finite Element Solution for Biopotentials: Erythrocyte in an Applied Field," IEEE Trans. Biomed. Eng., BME-35, pp. 712–718, 1988; and Tian Y. Tsong, "Molecular Recognition and Processing of Periodic Signals in Cells: Study of Activation of Membrane ATPases by Alternating Electric Fields," Biochimica et Biophysica Acta, 1113, pp. 53–70, 1992). Further, most aberrant or neoplastique cells exhibit substantial morphological deviation, in comparison to their non-transformed cellular stroma (David J. B. Ashley, Ed. "Evans' Histological Appearances of Tumors," Churchill Livingstone, New York, N.Y., 1978 and Catherine M. Keebler and James W. Reagan Ed., "A Manual of Cytotechnology," 6th Ed., American Society of Clinical Pathologists Press, U.S.A., 1983).

SUMMARY OF THE INVENTION

An object of the present invention is to provide a method for eliminating selected cancer cells or growth of cells (such as tumors) by time focusing electromagnetic fields upon the selected malignant sites.

Another object of the present invention is to disclose a method of achieving preferential necrosis of cells by either or both electroporation and electromagnetic interference with transmembrane enzyme activities.

A further object of the present invention is to supply an apparatus for time focusing a non-ionizing radiation field upon at least a portion of abnormal cells thereby inducing necrosis or preferential necrosis.

Still another object of the present invention is to disclose a method for preferential necrosis induction utilizing for electroporation a focused electromagnetic field, whereby a transmembrane potential of about 0.5 V to about 1.5 V is induced in the abnormal cells for a sufficient time period to cause necrosis of the abnormal cells resulting from the electroporation of each cell bilayer.

Yet a further object of the present invention is to relate a method for preferential necrosis induction utilizing, for electromagnetic transmembrane enzyme interference, an oscillating, focused electromagnetic field to induce a transmembrane potential of about 6 mV to about 20 mV in the abnormal cells for a sufficient time period and frequency so as to cause necrosis in the abnormal cells resulting from electromagnetic transmembrane enzyme interference.

Disclosed is a non-ionizing radiation emitting apparatus for preferential induction of cellular necrosis, comprising means for generating the non-ionizing radiation. Generally, the radiation is generated between opposing plates of poles. Also, provided are means for exposing cellular matter having both normal and abnormal cells to the non-ionizing radiation. Further, included are means for focusing effects of the non-ionizing radiation upon the abnormal cells thereby inducing necrosis preferentially upon the abnormal cells, wherein the non-ionizing radiation generating means generates the radiation at a level sufficient for the focusing means to produce necrosis of the abnormal cells via either electroporation or electromagnetic enzyme interference of the abnormal cells.

More specifically, first, the non-ionizing radiation generating means generates the radiation at a level sufficient for the focusing means to produce cellular transmembrane potentials ($\Delta\Psi M$) of about 0.5 V to about 1.5 V in the abnormal cells for a selected and sufficient time period to cause necrosis in the targeted abnormal cells via electroporation. Second, the non-ionizing radiation generating means generates the radiation at a level sufficient for the focusing means to produce a $\Delta\Psi M$ of about 6 mV to about 20 mV at the frequency specific to the transmembrane enzyme targeted (i.e. sodium potassium ATPase and the like) in the abnormal cells for a sufficient time period to cause necrosis in the abnormal cells via electromagnetic enzyme interference.

Specifically, the focusing means comprises means for moving, rotating, or translocating for a period of time the non-ionizing radiation generating means about an axis. Both a continuous and a pulsed radiation is contemplated to be within the realm of this disclosure. The rotation of the focused radiation causes effects induced by the non-ionizing radiation to converge to a point or zone containing at least a portion of the abnormal cells.

Also included in the subject invention is a method of inducing necrosis preferentially in abnormal cells. The subject method comprises generating non-ionizing radiation, focusing the non-ionizing radiation to a point location containing at least a portion of the abnormal cells, and maintaining the focused point of non-ionizing radiation for a period of time sufficient to induce necrosis of the abnormal cells by via either electroporation or electromagnetic enzyme interference of the abnormal cells. Usually, the non-ionizing radiation is generated between opposing plates or opposing poles. In the subject apparatus, the non-ionizing radiation is generated at a level sufficient to induce a $\Delta\Psi M$ of about 0.5 V to about 1.5 V in the abnormal cells for a sufficient time period to cause necrosis in the abnormal cells via the electroporation or the radiation is generated at a level sufficient to be focused to produce a $\Delta\Psi M$ of about 6 mV to about 20 mV in the abnormal cells for a sufficient time period to cause necrosis in the abnormal cells via electromagnetic enzyme interference. Additionally, as above with the subject apparatus, the focusing comprises positioning (via rotating, moving, translocating, and the like) for a period of time the opposing plates or the opposing poles about an axis thereby focusing the non-ionizing radiation exposure time to a point containing at least a portion of the abnormal cells, while maintaining the vectorial nature of the imposed field.

Other objects, advantages, and novel features of the present invention will become apparent from the detailed

DESCRIPTION OF THE PREFERRED EMBODIMENT

Figure 1:
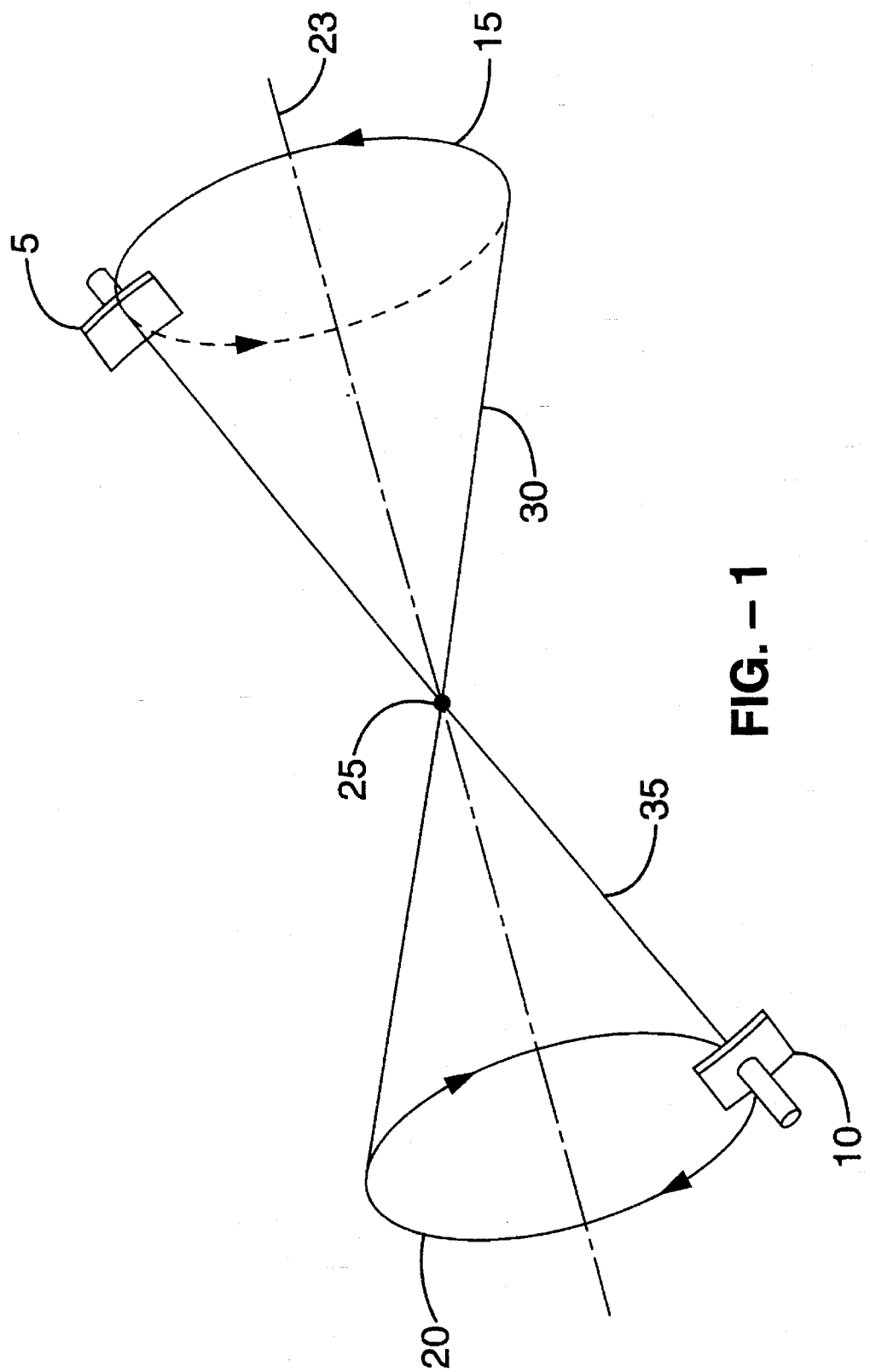
FIG. 1 is a perspective view of a low efficiency, equally divided, rotationally focused field.

The subject invention is directed towards the interaction of relatively low energy electromagnetic fields of generally non-ionizing radiation with closed cellular systems to produce cellular dystrophy or cell death. The non-ionizing radiation of the subject method for preferential necrosis or cancer therapy has fewer harmful side effects than those methods employing higher energy radiations. By utilizing focused low energy electromagnetic fields of the subject invention, cellular necrosis can be limited to the transformed cells within a particular locality, without soft tissue damage and, in general, the commonly observed free radical production produced by exposure to higher radiation.

The subject invention relies on non-ionizing electromagnetic radiation influencing at least one, if not both, of two membrane related phenomena. The two phenomena are both electromagnetically induced and morphologically dependent, namely electroporation and electromagnetic interference of transmembrane enzyme activities. The general concepts for both of these phenomena, in relation to the subject invention, are discussed immediately below.

Electroporation

Electroporation is the technique by which cell membranes are induced to dissociate by the generation of critical transmembrane potentials ($\Delta\Psi M$). The transmembrane potentials are generated by applying an electric field of low frequency and high field density until such time that a structural deformation of the cellular phospholipid bilayer occurs. It should be noted that the radiation levels required for the subject process are significantly lower than traditional high energy radiation treatments. The deformative process is, for the most part, vectorially unidirectional until the "rupture threshold" of the membrane is reached, after which the poration process begins. The rupture threshold is determined by the constitution and spatial orientation of the cell's membrane, as well as by the density of and time of exposure to the incident field. (Eberhard Neumann, Arthur E. Sowers, and Carol A. Jordan, "Electroporation and Electrofusion in Cell Biology," Plenum Publishing Company, New York, N.Y., 1989).

It must be emphasized that it is the morphological nature of the membrane that determines the critical time and field strength parameters of the rupture threshold. It is not just the potential applied to the cell, rather it is the transmembrane potential (an attenuated or amplified form of the applied field), that attains the critical threshold value for rupture.

It is important to understand the relationship between an applied field and the transmembrane field that is induced in the cell. The relationship is described or approximated by the Schwann Equation (Eberhard Neumann, Arthur E. Sowers, and Carol A. Jordan, "Electroporation and Electrofusion in Cell Biology," Plenum Publishing Company, New York, N.Y., 1989) for the spherical shell model of a cell. The geometry of the cell is simplified to two concentric spheres with a radial difference of 50 nm (the 50 nm separation approximates the thickness of the phospholipid membrane). Let $D_p$ represent the change in potential across the 50 nm membrane. Also, let l represent the internal spherical radius, E the applied field, $\omega$ the angular frequency of the field, and G the angle measured with respect to the normal of the cell membrane's surface. Letting $R_i$ represent the internal resistance, $R_e$ the external resistance, and $C_m$ the membrane capacitance.

$$D_p = (1.5[l][E]/[1+(\omega T)^2]^{0.5})\cos G \tag{1}$$

Where T is obtained by the following:

$$T = [l][C_m][R_i + (R_e/2)] \tag{2}$$

In order to initiate the electroporative process, it has been shown that the induced transmembrane potential must lie in the range of about 0.7 V to about 1.0 V or more generally between about 0.5 V and about 1.5 V (Eberhard Neumann, Arthur E. Sowers, and Carol A. Jordan, "Electroporation and Electrofusion in Cell Biology," Plenum Publishing Company, New York, N.Y., 1989). Given the relationship between the internal radius and the degree by which the imposed field is amplified, it follows that (if all cells were perfect spheres) certain malignant cells located in a specified area can be selectively destroyed; that is, preferential necrosis can be induced for those cells possessing the greatest "effective" radius.

If, for example, a four-dimensionally focused field (dimensions corresponding to time and the Cartesian set) is induced upon an area of the lymphatic system containing large cell lymphoma (allowing for spherical cell equivalents and letting the interstitial volume of the real cells determine the radii for the spherical shell models), a critical field strength can be found such that the majority of nontransformed lymphatic cells would be unharmed. Thus, necrosis would be induced only upon cells with effective radii greater than some predetermined value. Note that the greater the separation between the critical field strength and exposure time parameters of the transformed and nontransformed cells, the greater the feasibility of preferential poration.

Of course, real cells (in vivo) are not spherical, therefore a more realistic model needs to be used in order to approximate actual transmembrane potentials. Miller and Henriquez (Christine E. Miller and Craig S. Henriquez, "Three-Dimensional Finite Element Solution for Biopotentials: Erythrocyte in an Applied Field," IEEE Trans. Biomed. Eng., BME-35, pp. 712-718, 1988) presented an analysis of induced cell potentials using a three dimensional finite element solution.

Miller and Henriquez have proven an intuitive rationale or understanding that can be used to estimate relative field amplifications and, hence, the effectiveness of preferential electromagnetic field absorption. The relationship shown is that the lower the profile of the cell (incident to the field) and the smaller the cell volume, the stronger the induced field must be in order to attain the critical transmembrane potential. The subject invention utilizes this relationship as another possible means of necrosis specification for malignant cells with characteristic histological disorientations. Not only will cells with augmented interstitial volumes (as in the case of large cell lymphoma) undergo preferential poration, but any cells maintaining an unusually large surface profile incident to the field will hyper-amplify the applied electromagnetic field and, thus, be preferentially susceptible to the effects of electroporation. In terms of the cosG term in Equation (1) above, as the surface normal to the cell becomes perpendicular to the orientation of the E field, cosG approaches zero, hence, no surface potential is generated. Thus, it follows that no transmembrane potential or hyperpolarization will be induced upon the membrane present. Cells maintaining larger surface areas of exposure to the imposed field will be destroyed prior to those cells maintaining a diminished surface to field interface.

In relation to a cell's three dimensional orientation, given adequate time and an ample database, statistical trends in the size and growth patterns of transformed cells relative to their non-transformed counterparts sharing the same host tissue can be found. These trends will be utilized to limit membrane poration preferentially to transformed cells within the locale of focus. Thus, the unusual and necrosis useful orientations of transformed cells can be utilized to selectively kill those cells with minimal disturbance to the surrounding normal cells.

Many malignant forms of cells distort and become elongated exhibiting pleo-morphism, high n/c (nucleolus to cytoplasm ratio) ratios, and an overall increase in their cytoplasmic volume relative to the nontransformed cells located in the same locale. Such characteristics are typical of many forms of cancer. Note that, due to their size, if an electric field is induced parallel to the growth pattern of the tissue, the elongated cancer cells will maintain higher field-incident profiles than their non-transformed counterparts and would, thus, undergo poration at lower field intensities and shorter time intervals than the other cells in the same locality. Also, given a host tissue's common cell axial directive, cells that are not fully differentiated will not form within established tissue growth patterns and, therefore, will maintain a higher profile of exposure to the field. This relies on the condition that the field can be induced parallel to the common axis of tissue growth.

Most cancer cells with augmented interstitial volumes seem to maintain growth patterns that would allow them to be preferentially attacked by electroporative techniques. The reason for this would seem to be two-fold. First, it is the nature of the disorder, in that, most (although not all) forms of cancer lack the tissue coordinating ability to significantly differentiate, thus producing growth patterns atypical of the tissue. Second, most nonmalignant tissues maintain low entropy stacking systems with a common cellular alignment; the malignant growth is thus forced to "pack" itself in a highly entropic manner because of its different morphological characteristics (i.e., size, form, etc.). Transformed cells maintain higher tissue-relative profiles. Hence, given the ability to determine, focus and align the appropriate uniform field strengths, electroporative techniques can be employed to preferentially eliminate many forms of cancer cells from their host tissue, simply on the basis of their growth patterns and size.

Electromagnetic Enzyme Interference

Some forms of cancer (e.g., small cell carcinoma) have a substantial decrease in interstitial volume, thus rendering the nontransformed counterparts preferentially vulnerable to porative degradation in the presence of a field; electroporative therapy is thereby limited and contraindicated. It is in such cases that another form of bio-electromagnetic control seems even more promising: electromagnetic interference of membrane-bound enzyme activities.

Many membrane-bound enzymes have been observed in vitro to interact with imposed electric fields in a variety of ways (Tian Y. Tsong, "Molecular Recognition and Processing of Periodic Signals in Cells: Study of Activation of Membrane ATPases by Alternating Electric Fields," Biochimica et Biophysica Acta, 1113, pp. 53–70, 1992). In most cases, if the transmembrane potential (induced by an applied electric field) attains a specified amplitude neither above nor below that which is critical to the optimal response of the targeted enzyme, some form of metabolic alteration can be induced. Furthermore, not only can the metabolic activity of the enzyme be selectively altered on the basis of its critical transmembrane potential; but each enzyme also exhibits maximal and minimal responses in correlation to the frequency of the applied field (Tian Y. Tsong, "Molecular Recognition and Processing of Periodic Signals in Cells: Study of Activation of Membrane ATPases by Alternating Electric Fields," Biochimica et Biophysica Acta, 1113, pp. 53–70, 1992 and Dao-Sheng Liu, R. Dean Astumain, and Tian Yow Tsong, "Activation of $Na^+$ and $K^+$ Pumping Modes of (Na, K)-ATPase by an Oscillating Electric Field," Journal of Biological Chemistry, Vol. 265, No. 13, pp. 7260–7267, 1991). One example of such a membrane-bound enzyme (found in almost every cell type throughout the body) is sodium potassium ATPase.

Laboratory investigations by Tsong (Dao-Sheng Liu, R. Dean Astumain, and Tian Yow Tsong, "Activation of $Na^+$ and $K^+$ Pumping Modes of (Na, K)-ATPase by an Oscillating Electric Field," Journal of Biological Chemistry, Vol. 265, No. 13, pp. 7260–7267, 1991 and Engin H. Serpersu and Tian Yow Tsong, "Activation of Electrogenic $Rb^+$ Transport of (Na, K)-ATPase by the Electric Field," Journal of Biological Chemistry, Vol. 259, No. 11, pp. 7155–7162, 1984) indicated that at 4° C. when erythrocytes, in suspension, were exposed to an AC field of amplitude 20 V/cm (creating a transmembrane potential of 12 mV) and a frequency of 1 kHz, activation of the potassium influx "mode" of the sodium potassium ATPase was shown to be at an optimum. Without the characteristic ATP consumption, the sodium potassium ATPase becomes metabolically coupled to the oscillatory field and foregoes its normal role of effluxing three sodium ions for every two potassium ions influxed. Under such conditions, it functions solely to influx the potassium ion. Tsong demonstrated this decoupled state (in vitro), but the subject invention will be utilized in vivo, thereby generating a form of localized sodium efflux inhibition.

Most cancer cells have been shown to require a sodium efflux rate higher than their nontransformed correlates. If the sodium potassium ATPase fails to efflux sufficient quantities of the sodium ion, interstitial osmoregularity cannot be maintained (Bohinski, "Modern Concepts in Biochemistry," 5th Ed., Allyn and Bacon, Inc., Newton, Mass., 1987). Consequently, the cell would be subjected to hyperosmotic swelling, followed by rupture. Further, the subject electromagnetic irradiation process will decouple the sodium potassium ATPase from its normal role of ATP hydrolysis. Given the dependence of the other metabolic pathways upon the proper functioning of this process, e.g., the glucose active transport mechanism, some form of terminal metabolic inhibition should occur.

The transmembrane potentials required to induce these types of enzymatic phenomena typically range from about 6 to about 20 millivolts (Tian Y. Tsong, "Molecular Recognition and Processing of Periodic Signals in Cells: Study of Activation of Membrane ATPases by Alternating Electric Fields," Biochimica et Biophysica Acta, 1113, pp. 53–70, 1992) (a voltage far less than the about 0.7 to about 1 volt required to induce electroporative effects, noted above). This would suggest that cancer cells could theoretically be targeted, even if they maintain a diminished surface/field profile relative to the nontransformed cells in their immediate surroundings. Those that are larger than the targeted aberrant cells, though hyperamplifying the applied field, should remain virtually unharmed. In fact, cells amplifying the applied potential either above or attenuating below the transmembrane value (critical to a optimum enzymatic response window), should remain undamaged.

Hence, with the selection of proper field strengths and frequencies, a low energy electric field can induce electro-enzymatic degradation of transformed cells while posing a minimal amount of disruption to proximal nontransformed cells. This technique would not only provide for morphometric selectivity, but the variety of enzymes from which the oncologist can choose would afford a means of treatment specification relative to the enzymatic content of the malignancy's host organ or tissue.

EXPERIMENTAL

EXAMPLE 1. DATA COLLECTION 1

In order to test for any statistical trends in morphometric alterations of transformed tissues (in vivo), a substantial database must be established and recorded. A collection of pathological and cytological data will be conducted. Using methods of morphometric analysis, comparative assays will be performed for transformed and nontransformed interstitial cell volumes. Although variations on the following list is contemplated, tissue samples from the same host, containing both malignant and nonmalignant cell types, will be systematically categorized by the following criteria:

1) Origin of tissue and stage of development;

2) Identification method used for determination of malignancy;

3) Separative identification method used to distinguish nonmalignant cells from malignant;

4) n/c ratio of malignant cells;

5) n/c ratio of nonmalignant cells;

6) The number of sample cells shown on the slide;

7) The percentage of sample cells diagnosed malignant;

8) The average interstitial volume of the nontransformed cells;

9) The average interstitial volume of transformed cells;

10) The standard deviation of the mean cell volume; and

11) Estimation of error in the determination of the above values.

Enough cellular information is currently available (and can be augmented with additional data) to predict acceptable growth patterns in vivo (pending the origin and cell type of the host tissue) ( David J. B. Ashley, Ed. "Evans' Histological Appearances of Tumors," Churchill Livingstone, New York, N.Y., 1978, Catherine M. Keebler and James W. Reagan Ed., "A Manual of Cytotechnology," 6th Ed., American Society of Clinical Pathologists Press, U.S.A., 1983, James F. Holland, Emil Frei III, Robert C. Bast Jr., Donald L. Morton, Donald W. Kufe and Ralph R. Weichselbaum, Eds., "Cancer Medicine," 3rd Ed., Vol. 1 & 2, Lea & Febiger, Pa. 1993, and Emanuel Rubin and John L. Farber, Ed., "Pathology," J. B. Lippincott Company, Philadelphia, Pa., 1988).

In vivo testing of the subject invention is preferred. Constitutional changes in the cells brought about by metabolic cessation and atmospheric exposure (for in vitro testing) would both limit the accuracy and increase the time constraints of the procedures involved. In addition, the presence of electrokinetically generated fields caused by pulsatile blood flow must be taken into account. An absence of these fields would generate non-comparative data, e.g., between tissues containing high and low capillary densities, thus limiting the scope of our statistical analysis.

EXAMPLE 2. DATA COLLECTION 2

The following data obtaining steps will be performed:

1) A needle biopsy will be taken from both the targeted tumor and the surrounding tissue. From the cells sampled, an average cell morphology will be approximated;

2) Three-dimensional topological scans of the host's target site will be performed using either P.E.T. scans, magnetic resonance imaging, or any available method with comparable resolution;

3) The scans will be made in cross-sectional slices (in the case of P.E.T.) every 30°;

4) A three dimensional composite will be made of the targeted tumor;

5) Two insulated needle electrodes will be inserted (postanasthetically) into the host. While maintaining the specified distance between the electrodes, one needle is to be inserted into the tumor, and the other beyond the periphery of the malignancy;

6) Using the morphological samples to evaluate the theoretical supercritical field strengths, a voltage will be provided to the two electrode system in order to induce electroporative degradation;

7) Postoperative, the animal will again be analyzed by the technique specified in step 2;

8) If steps 2 through 5 are repeated incrementally, increasing the applied voltage from below the theoretical critical voltage to supercritical levels, tissue necrosis should be observed only at coordinates of maximum field density. Thus, calculated estimates can be compared to those actually observed with in vivo conditions.

By performing the above procedures, three criteria of primary relevance to the above subject invention are addressed. First, a comparison of necrosis patterns to predicted areas of supercritical field strength will allow some determination of both macro and microbiological field parameters. Second, methods of predicting the mean transmembrane field amplification will be evaluated as to their accuracy and precision. Finally, given an adequate amount of supporting data from the previous two criteria, the subject preferential necrosis method will be performed.

EXAMPLE 3. VOLTAGE SCAN VIA E-FIELD ROTATION

To date, noninvasive electroporative or electromagnetic enzyme interference applications have not been attempted in vivo largely due to the physical difficulties of efficiently concentrating a low frequency electric field at a finite point in a living host. These difficulties stem, in part, from the sheer complexity of the capacitive system analysis. A feasible electroporative or electromagnetic enzyme interference device requires a dramatic field convergence within a volume of about one to about five $cm^3$. With a subject field generating apparatus, the voltage scan method focuses in four dimensions or time focused (the three normal space coordinates and an added time element of focusing whereby the electromagnet field is rotationally scanned over a period of time to cause a point or at least zone focusing) a three dimensional field (normal space coordinates). One manner to produce a required three dimension electromagnetic field is to utilized shaped capacitive plates or equivalent objects. However, it is noted here and further below, that it may be more feasible than using capacitive plates to use the component E generated by a focused B field as a source for focused electromagnetic fields. Therefore, the noted plates 5 and 10 or 40 and 45, depicted in FIGS. 1 and 2, respectively, are capacitive plates or the poles of a suitable configured electromagnet.

The epidermis is a highly insulative and strongly absorptive tissue (Kronig, R. Ed., Physics, Pergamon Press Ltd., London, page 798, 1954). Also, musculoskeletal tissues have been shown to exhibit strong absorption of such fields (Lee, R. C., River, L. P., Pan, F. S., Ji, L. and Wollman, R. L., Proceedings of the National Academy of Sciences, 89(10):4524–4528, 1992). Wherever a field passes through tissues extralocated to or surrounding the targeted area of irradiation, strongly absorptive properties will enhance unwarranted cellular necrosis. The voltage scan method is a technique which improves the limited focusing of low energy E fields by concentrating the necrotic breakdown of tissues over time.

For example only, to explain the voltage scan method, consider a simple model having two points within the thigh of a human leg. One point A is located relatively close to the femur and is representative of the stereotaxic location of a metastically-induced lymphatic tumor. Consider the second point B located closer to the epidermis. This second point shall represent any one of an infinite number of cell groups which can be located between the nearest field generative device and point A. The purpose of such a model is to embody the theoretical parameters (in a simplified fashion) that must be overcome in order to cause cellular necrosis at cancer containing point A and not at normal tissue point B. If only an external source E field directed across points A and B was utilized, one would observe that, given the higher voltages existing proximal to the field generators, necrosis would be induced primarily at the epidermis, secondarily at point B, tertiarily and least significantly at the desired point of necrosis, point A.

While some of the field absorption of the epidermis can be attenuated by soaking of the skin in isotonic salt solution, any point between the field generator and the target point A will receive higher voltage field exposure than point A. This will always be true regardless of the mechanism of field generation (capacitive or B field component). In the capacitive case, some field convergence can be induced by the physical shaping of the positive and negative plates. Due to the relatively high distance that would be required between the plates (to accommodate an arm, leg, and the like), however, any induced convergence will be slight and only regional in the low frequency E field case.

For cellular necrosis, electroporation requires a greater amount of energy than does electromagnetic enzyme interference. Therefore, even though both electroporation and electromagnetic enzyme interference can be achieved with the voltage scan method, for illustrative purposes, electroporation will be discussed. Further, using this simplified leg model, the voltage scan method can induce point, or at least zonal electroporation. Electroporation is induced by supercritical transmembrane potentials ($\Delta\Psi M$). As noted above, electroporation induced preferential necrosis is proportional to the strength of the applied field, cell geometry, and to the cosine of the angle of radiant incidence relative to the cell surface normal. The voltage scan method uses the angular, time and field voltage dependencies to induce localized electroporative effects.

Referring once again to the leg model, a form of in vivo noninvasive electroporation must be able to induce localized electroporative effects at point A and not at point B. The voltage scan method increases the amount of cell membrane deformation by building the $\Delta\Psi M$ through successive field exposures (by rotating the electric field source) which maintains the same angular relationship to the arbitrary surface normal of the tumor being attacked. Successive exposures from variant localities (a rotational continuum is possible), maintaining the same angular attack, create an effective supercritical exposure time at the desired point A, not at point B. Although the scanning process can be by stepped increments, and is so noted as an embodiment of the subject invention, the optimum form of achieving this voltage scan method allows the positive and negative capacitive plates or equivalent objects to follow a rotational time course pattern resembling two cones interfaced with one another (see FIG. 1).

Specifically, as seen in FIG. 1, the two plates 5 and 10 are rotated in equally sized (same diameter of rotation) paths 15 and 20 about a central axis 23. Although the paths 15 and 20 are illustrated as being circular, other shapes such as elliptical and the like are acceptable. By allowing the electromagnetic field to rotate, the field is focused at a desired location point or zone 25 via two opposing cones 30 and 35. Tissues located away from the focal point 25 (at the epidermis and proximal tissues) have limited exposure times to supercritical electromagnetic field levels and, due to the limited exposure times, will not electroporate.

In order to induce cellular electroporation, the $\Delta\Psi M$ must be maintained at about 0.5 V to about 1.5 V for about micro to millisecond time durations (Weaver, James C., "Electroporation: A general Phenomenon for Manipulating Cells and Tissues," Journal of Cellular Biochemistry, 51:426–435, 1993). Maintaining a lower $\Delta\Psi M$, in the range of about 0.2 V to about 0.5 V, requires exposure times in excess of about 0.1 milliseconds (also, Weaver, James C., "Electroporation: A general Phenomenon for Manipulating Cells and Tissues," Journal of Cellular Biochemistry, 51:426–435, 1993). So, by creating a slight central field convergence in addition to limiting exposure times of non-targeted cells to under microsecond time durations, one can effectively sculpt regions of higher electroporative susceptibility concentric to the point of conic intersection 25.

Usually, plate charge kinetics does not allow for the complete charging, discharging and field generative process to occur in under microsecond time durations, considering the magnitude of the voltages required. Using a stagnant field, however, and shuttering or rotating that field directive so that the primary area of field convergence migrates its own cross-sectional distance in under a microsecond, the voltage scan method will cause electroporation at the focal point 25.

Figure 2:
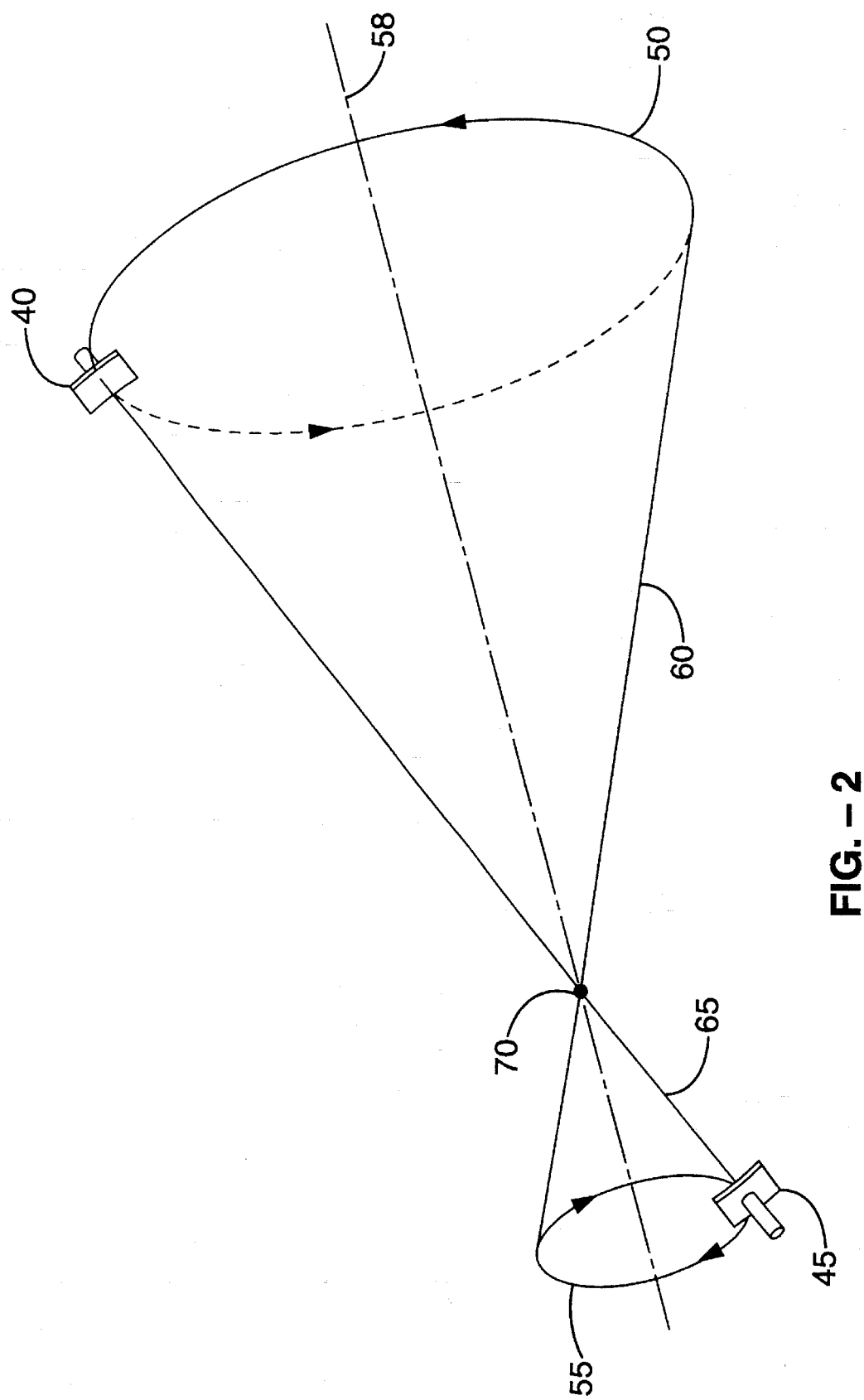
FIG. 2 is a perspective view of a high efficiency, non-equally divided, rotationally focused field.

Returning to the simple leg model noted above, for increased efficiency, point A (the point to be electroporated or treated generally with non-ionizing electromagnetic radiation), however, cannot simply be located at the point of equidistant conic intersection (with the least efficient location noted in FIG. 1). As illustrated in FIG. 2, it is critical for increased efficiency that the cones which represent the time course of travel taken by the electrodes are not of the same height. If the two cones are of the same height, then the point of conic intersection will be exposed to lessened field voltages. Rather, if the cones are offset as much as possible, the point of conic intersection will maintain higher voltage strengths since its relative location to the two field generating plates is unequal. Furthermore, if the distance of the point of conic intersection from the closest located capacitive plate is represented by "X" and if the total distance between the two plates is represented by "Y", the smaller the quotient of "X" over "Y", the smaller the difference between the critical exposure times for point A and B in the leg model.

Specifically, as seen in FIG. 2, the two plates 40 and 45 are rotated in non-equally sized (different diameters of rotation) paths 50 (larger diameter path) and 55 (smaller diameter path) about a central axis 58. Although the paths 50 and 55 are illustrated as being circular, other shapes such as elliptical and the like are acceptable. By allowing the electromagnetic field to rotate, the field is time focused at a desired location point or zone 70 via the two unequally sized and opposing cones 60 and 65. As with the equally sized cone version illustrated in FIG. 1, tissues located away from the focal point 70 (at the epidermis and proximal tissues) have limited exposure times to supercritical and subcritical electromagnetic field levels and will not electroporate.

EXAMPLE 4. VOLTAGE SCAN VIA B-FIELD ROTATION

A B-field includes an E-field component, therefore, the focused B-field indirectly focuses the necessary E-field for the desired cellular necrosis. A rotated B-field (or several B-fields individually intersecting at a desired point) focused at a single point (as described above for the capacitive plate equivalent) gives rise to supercritical, E-field strengths. Further, B-fields are generally easier to focus at a narrow or point location than E-fields.

Additionally, the above described methods for induction of preferential necrosis may be utilized in combination with now known or latter developed technologies that assist in the necrosis induction process:

The invention has now been explained with reference to specific embodiments. Other embodiments will be suggested to those of ordinary skill in the appropriate art upon review of the present specification.

Although the foregoing invention has been described in some detail by way of illustration and example for purposes of clarity of understanding, it will be obvious that certain changes and modifications may be practiced within the scope of the appended claims.

What is claimed is:

1. A non-ionizing radiation emitting apparatus for preferential induction of cellular necrosis, comprising:
   a) means for generating the non-ionizing radiation;
   b) means for exposing cellular matter having both normal and abnormal cells to the non-ionizing radiation; and
   c) means for focusing the non-ionizing radiation upon said abnormal cells thereby inducing necrosis preferentially in said abnormal cells.

2. A cellular necrosis induction apparatus according to claim 1, wherein the non-ionizing radiation generating means generates the radiation between opposing plates of poles.

3. A cellular necrosis induction apparatus according to claim 1, wherein said non-ionizing radiation generating means generates the radiation at a level sufficient for said focusing means to produce necrosis of said abnormal cells via either electroporation or electromagnetic enzyme interference of said abnormal cells.

4. A cellular necrosis induction apparatus according to claim 1, wherein said non-ionizing radiation generating means generates the radiation at a level sufficient for said focusing means to produce necrosis of said abnormal cells by electroporation.

5. A cellular necrosis induction apparatus according to claim 1, wherein said non-ionizing radiation generating means generates the radiation at a level sufficient for said focusing means to produce necrosis of said abnormal cells by electromagnetic enzyme interference of said abnormal cells.

6. A cellular necrosis induction apparatus according to claim 1, wherein said non-ionizing radiation generating means generates the radiation at a level sufficient for said focusing means to produce a transmembrane voltage of about 0.5 V to about 1.5 V in said abnormal cells for a sufficient time period to cause necrosis in said abnormal cells via electroporation.

7. A cellular necrosis induction apparatus according to claim 1, wherein said non-ionizing radiation generating means generates the radiation at a level sufficient for said focusing means to produce a transmembrane voltage of about 6 mV to about 20 mV in said abnormal cells for a sufficient time period to cause necrosis in said abnormal cells via electromagnetic enzyme interference.

8. A cellular necrosis induction apparatus according to claim 1, wherein said focusing means comprises means for rotating for a period of time said non-ionizing radiation generating means about an axis thereby focusing the non-ionizing radiation to a point containing at least a portion of said abnormal cells.

9. A non-ionizing radiation emitting apparatus for preferential induction of cellular necrosis, comprising:
   a) means for generating the non-ionizing radiation, wherein the radiation is generated between opposing plates of poles;
   b) means for exposing cellular matter having both normal and abnormal cells to the non-ionizing radiation; and
   c) means for focusing the non-ionizing radiation upon said abnormal cells thereby inducing necrosis preferentially in said abnormal cells, wherein said non-ionizing radiation generating means generates the radiation at a level sufficient for said focusing means to produce necrosis of said abnormal cells via either electroporation or electromagnetic enzyme interference of said abnormal cells.

10. A cellular necrosis induction apparatus according to claim 9, wherein said non-ionizing radiation generating means generates the radiation at a level sufficient for said focusing means to produce a transmembrane voltage of about 0.5 V to about 1.5 V in said abnormal cells for a sufficient time period to cause necrosis in said abnormal cells via electroporation.

11. A cellular necrosis induction apparatus according to claim 9, wherein said non-ionizing radiation generating means generates the radiation at a level sufficient for said focusing means to produce a transmembrane voltage of about 6 mV to about 20 mV in said abnormal cells for a sufficient time period to cause necrosis in said abnormal cells via electromagnetic enzyme interference.

12. A cellular necrosis induction apparatus according to claim 9, wherein said focusing means comprises means for rotating for a period of time said non-ionizing radiation generating means about an axis thereby focusing the non-ionizing radiation to a point containing at least a portion of said abnormal cells.

13. A method of inducing necrosis preferentially in abnormal cells, comprising the steps of:

a) generating non-ionizing radiation;

b) focusing said non-ionizing radiation to a point location containing at least a portion of the abnormal cells; and c) maintaining said focused point of non-ionizing radiation for a period of time sufficient to induce necrosis of the abnormal cells by via either electroporation or electromagnetic enzyme interference of said abnormal cells.

14. A method for preferential necrosis induction of abnormal cells, according to claim 13, wherein said generating of said non-ionizing radiation is between opposing plates or opposing poles.

15. A method for preferential necrosis induction of abnormal cells, according to claim 14, wherein said focusing comprises rotating for a period of time said opposing plates or said opposing poles about an axis thereby focusing said non-ionizing radiation to a point containing at least a portion of the abnormal cells.

16. A method for preferential necrosis induction of abnormal cells, according to claim 13, wherein said generating of said non-ionizing radiation is at a level sufficient for said focusing and producing a transmembrane voltage of about 0.5 V to about 1.5 V in said abnormal cells for a sufficient time period to cause necrosis in said abnormal cells via said electroporation.

17. A method for preferential necrosis induction of abnormal cells, according to claim 13, wherein said generating of said non-ionizing radiation is at a level sufficient for said focusing and producing a transmembrane voltage of about 6 mV to about 20 mV in said abnormal cells for a sufficient time period for causing necrosis in said abnormal cells via said electromagnetic enzyme interference.

18. A method of inducing necrosis preferentially in abnormal cells, comprising the steps of:

a) generating non-ionizing radiation between opposing plates or opposing poles;

b) focusing said non-ionizing radiation to a point location containing at least a portion of the abnormal cells, wherein said focusing comprises rotating for a period of time said opposing plates or said opposing poles about an axis thereby focusing said non-ionizing radiation to a point containing at least a portion of the abnormal cells; and c) maintaining said focused point of non-ionizing radiation for a period of time sufficient to induce necrosis of the abnormal cells by via either electroporation or electromagnetic enzyme interference of said abnormal cells.

19. A method for preferential necrosis induction of abnormal cells, according to claim 18, wherein said generating of said non-ionizing radiation is at a level sufficient for focusing and producing a transmembrane voltage of about 0.5 V to about 1.5 V in said abnormal cells for a sufficient time period for causing necrosis in said abnormal cells via said electroporation.

20. A method for preferential necrosis induction of abnormal cells, according to claim 18, wherein said generating of said non-ionizing radiation is at a level sufficient for focusing and producing a transmembrane voltage of about 6 mV to about 20 mV in said abnormal cells for a sufficient time period for causing necrosis in said abnormal cells via said electromagnetic enzyme interference.

* * * * *